(12) United States Patent
Kuo et al.

(10) Patent No.: US 7,672,714 B2
(45) Date of Patent: Mar. 2, 2010

(54) MINIATURE WIRELESS APPARATUS FOR COLLECTING PHYSIOLOGICAL SIGNALS

(75) Inventors: Terry B. J. Kuo, 7F-2, No. 52, Beichang 5th St., Ji-An Township, Hualien County 973 (TW); Cheryl C. H. Yang, 7F-2, No. 52, Beichang 5th St., Ji-An Township, Hualien County 973 (TW)

(73) Assignees: Terry B. J. Kuo, Ji-An Township, Hualien County (TW); Cheryl C. H. Yang, Ji-An Township, Hualien County (TW); Enjoy Research Inc., Ji-An Township, Hualien County (TW)

( * ) Notice: Subject to any disclaimer, the term of this patent is extended or adjusted under 35 U.S.C. 154(b) by 714 days.

(21) Appl. No.: 11/462,103

(22) Filed: Aug. 3, 2006

(65) Prior Publication Data

US 2007/0167848 A1    Jul. 19, 2007

(30) Foreign Application Priority Data

Nov. 28, 2005   (TW) ................................. 9414168 A
Jan. 13, 2006   (TW) ................................. 9510326 A

(51) Int. Cl.
*A61B 5/02* (2006.01)

(52) U.S. Cl. ..................................................... 600/509

(58) Field of Classification Search ................ 600/308, 600/391, 485, 509; 607/60, 118
See application file for complete search history.

(56) References Cited

U.S. PATENT DOCUMENTS 6,038,464 A * 3/2000 Axelgaard et al. ........... 600/391
2001/0014556 A1* 8/2001 Jones et al. .................. 439/632
2003/0109905 A1* 6/2003 Mok et al. .................... 607/60

OTHER PUBLICATIONS

Kuo, Terry; et al., "Effect of aging on gender differences in neural control of heart rate", the American Journal of Physiology, 1999, H2233-H2239, the American Physiological Society, Bethesda MD.
Kuo, Terry; et al., "Sexual dimorphism in the complexity of cardiac pacemakre activity", the American Journal of Physiology, Oct. 2002, H1695-H1702, vol. 283, the American Physiological Society, Bethesda MD.

* cited by examiner

*Primary Examiner*—Carl H Layno
*Assistant Examiner*—Luther G. Behringer
(74) *Attorney, Agent, or Firm*—Egbert Law Offices PLLC

(57) ABSTRACT

A miniature wireless apparatus for collecting physiological signals comprises an electrode pair, an amplifier module, a microcontroller, a wireless module, and a battery. The electrode pair collects a pair of physiological signals of a person under test. The amplifier module amplifies the pair of physiological signals. The microcontroller performs an analog-to-digital conversion and a data compression for an amplified physiological signal generated by the amplifier module. The wireless module modulates a digital physiological signal generated by the microcontroller and transmitting the modulated digital physiological signal to a receiver at the far end. The apparatus can be implemented by a structure of multilayered circuit boards. With the progress of semiconductor technology, all the components of the miniature wireless apparatus can be further integrated to one circuit board, or even one chip.

2 Claims, 7 Drawing Sheets

MINIATURE WIRELESS APPARATUS FOR COLLECTING PHYSIOLOGICAL SIGNALS

RELATED U.S. APPLICATIONS

Not applicable.

STATEMENT REGARDING FEDERALLY SPONSORED RESEARCH OR DEVELOPMENT

Not applicable.

REFERENCE TO MICROFICHE APPENDIX

Not applicable.

FIELD OF THE INVENTION

The present invention is related to an apparatus for collecting physiological signals, and more specifically to a miniature wireless apparatus for collecting physiological signals.

BACKGROUND OF THE INVENTION

Physiological signals include heartbeat, brainwaves, breath, body temperature, and so on. All these physiological signals are signs of health, and if the related information of the physiological signals can be obtained easily, it helps a lot to take care of patients, the labor cost can be reduced and the quality of medical care can be improved.

FIG. 1 illustrates an electrocardiogram (ECG) signal of the heartbeat. Generally speaking, the Q-S interval is called QRS wave, wherein the point of the QRS turning upwardly is point Q, the peak is point R, and the final lowest point of the QRS is called point S. In the discrimination procedure of QRS, firstly the peak inspection procedure is performed to find out QRS in the physiological signal, and then parameters such as the amplitude and duration of the QRS wave are measured, and the average value and the standard deviation of the parameters are calculated to serve as the standard template. Thereafter, each QRS wave is compared with the template.

The heart rate variability (HRV) analysis is a method of analyzing the heart's physiological function from the heartbeat interval sequence. The standard analysis procedure was defined by the European and American Heart Association in 1996 (Task Force of the European Society of Cardiology and the North American Society of Pacing and Electrophysiology, 1996), and later, it was modified (Kuo et al., 1999) in some parts, and the principles are substantially illustrated as follows.

(1) First the information of the heartbeat interval is acquired mainly by defining the onset of each heartbeat from the R wave in the ECG, and the interval between each R wave and the next R wave is a heartbeat interval RR.

(2) If the significant amplitude fluctuation exists in the continuous RR sequence, for example, more than three standard deviations, it may be arrhythmias or noise. If it is arrhythmias, the subject must be warned immediately, since the life of the subject is threatened. If it is noise, the analysis technique must be improved to eliminate the noise.

(3) If the significant amplitude fluctuation does not appear in the successive RR sequence, a more exact numerical analysis is carried out on the RR sequence, which includes frequency spectrum analysis (Kuo et al., 1999) and nonlinear analysis (Kuo & Yang, 2002) etc.

The sleep stages can be distinguished according to the brain waves, the electromyography, and the oculomotor signal. If the partition of sleep stages can be easily carried out, the prevention of many sleep-related diseases can be easily realized. The measurement of the brain waves can reveal many diseases, e.g., epilepsy and Alzheimer's disease. If the measurement of breathing signals is added, diseases of sleep breathing-related such as obstructive sleep apnea syndrome can be found. Further, if the heart rate or HRV analysis is added, the connection between sleep and high blood pressure can be comprehend. The sleep physiological signal monitor and analysis are indispensable physiological signals in clinical medicine. The popularization of the measurement of the signals is helpful in prevention, monitor and diagnosis of diseases.

Most of the apparatuses for collecting physiological signals require more than one wire. Although the signal is exact, a lot of electrical wires must be connected to the subject, and the subject cannot move under examination, so that it is time-consuming to connect the wires and inconvenient for the subject. Recently, along with the progress of science and technology, semiconductor and wireless transmission technologies have become well developed, and the miniature products for detecting physiological signals have been proposed successively. A so-called ambulatory physiological signal-collecting apparatus has been achieved that is the size of a palm. Some of the apparatuses can continuously store the physiological signals in an internal memory, and some of the apparatuses can transmit the physiological signals to a remote receiver in the form of wireless wave or the IR transmission in real time, so that the health condition of the subject can be acquired in real time outside. The technologies allow the application of the physiological signal detection to be more convenient and flexible. However, the instruments are big and too heavy, and especially, the manner of connecting the wire is too complex for persons who have no training. Although the electrical wires are short, it is also inconvenient for users. Therefore, currently, ambulatory physiological signal-collecting instruments are still used as medical instruments, and the instrument wearing must be done under the instruction of experts. Therefore, the instruments are not consumable electronic products that can be freely used by common people.

In order to spread the physiological signal analysis technology widely to each family and person, it is necessary to overcome the inconvenience of various fixed or portable physiological instruments, and miniaturization and completely wireless instruments inevitably become the direction to follow in development.

BRIEF SUMMARY OF THE INVENTION

The present invention discloses a miniature wireless apparatus for collecting physiological signals, and the apparatus comprises an electrode pair, an amplifier module, a microcontroller, a wireless module and a battery.

The electrode pair comprises a positive electrode and a negative electrode to collect a pair of physiological signals of a person under test. The amplifier module is used for amplifying the pair of physiological signals. The microcontroller comprises an analog-to-digital (A/D) conversion unit connected to the amplifier module and a digital signal processing (DSP) unit connected to the analog-to-digital conversion unit, wherein the analog-to-digital conversion unit is used for performing a sampling and an analog-to-digital conversion for an amplified physiological signal generated by the amplifier module. The digital signal processing unit is used for performing a data compression for a digital physiological signal generated by the analog-to-digital conversion unit. The wireless module comprises a modulator/demodulator and a wireless transceiver. The modulator is used for modulating the digital physiological signal compressed by the digital signal-processing unit to generate a modulated digital physiological signal, and the wireless transceiver is used for transmitting the modulated digital physiological signal to a receiver at the far end. Meanwhile, the wireless transceiver also receives a wireless signal from the far end.

The miniature wireless apparatus can be implemented by a structure of multilayered circuit boards. With the progress of semiconductor technology, all the components of the miniature wireless apparatus can be further integrated into one circuit board, or even one chip.

The miniature wireless apparatus can further comprise a positive electrode patch and a negative electrode patch, wherein the positive electrode patch and the negative electrode patch are electrically connected to the positive electrode and the negative electrode through an electric contact point respectively.

The positive electrode patch and negative electrode patch may further comprise a conductive film respectively. The conductive film can be designed with double-sided adhesive; one side is adhered to the electrode patch and the other side is adhered to the body surface of the person under test to generate the conductive contact, so as to collect the physiological signals.

The miniature wireless apparatus for collecting physiological signals can further comprise an outer waterproof film or an outer waterproof cover, such that the person under test feels free in doing various activities.

The miniature wireless apparatus is applied to collect an electroencephalogram signal, an electrooculogram, a forehead or body temperature signal, an electrocardiogram (ECG) signal, an electromyogram signal, a nasal breath or a breathing signal.

The miniature wireless apparatus of the present invention comprises the following advantages:

(1) The apparatus is wireless and small in volume, so it is convenient to carry and use.
(2) Since the material of the apparatus in use is simple, the cost of mass production is reduced, thus satisfying the requirements for disposable medical supplies, and is suitable for monitoring patients with highly infectious diseases.
(3) The person under test feels free in doing various activities due to the waterproof design.
(4) The conductive film can be often changed, thus preventing skin inflammation of the person under test caused by long-term contact.

DETAILED DESCRIPTION OF THE INVENTION

Figure 1:
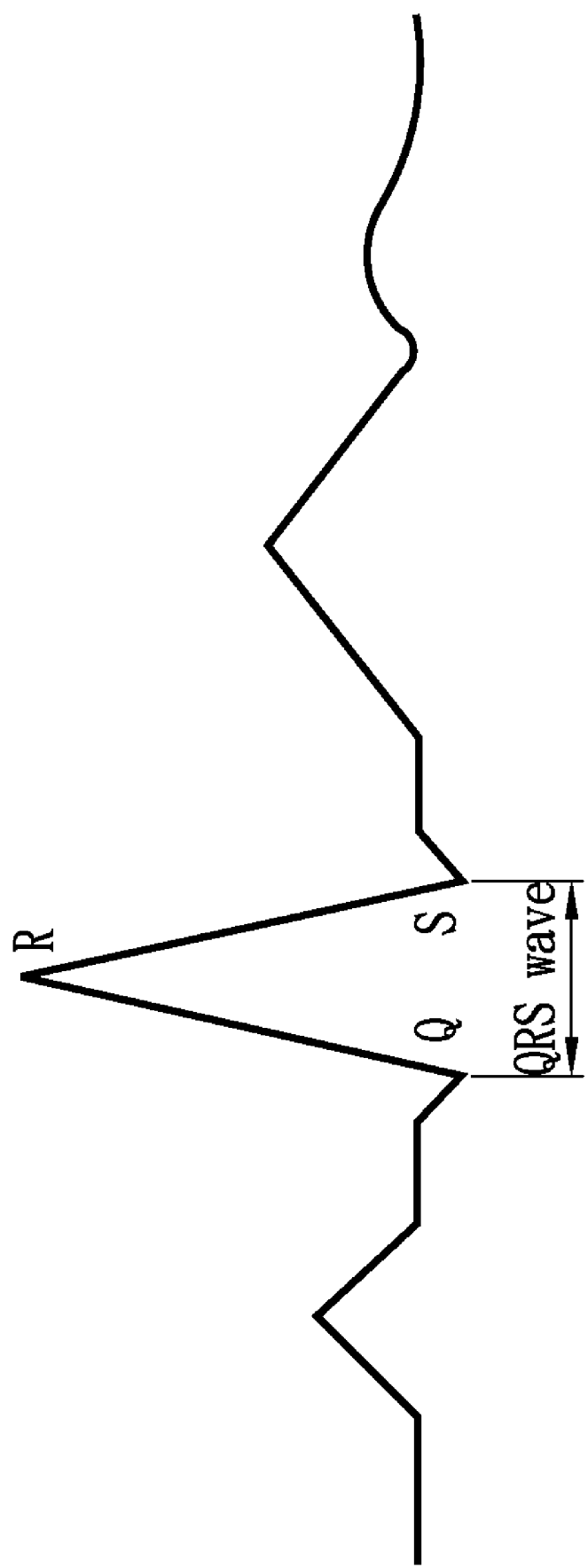
FIG. 1 illustrates an electrocardiogram signal of the heartbeat.
Figure 2:
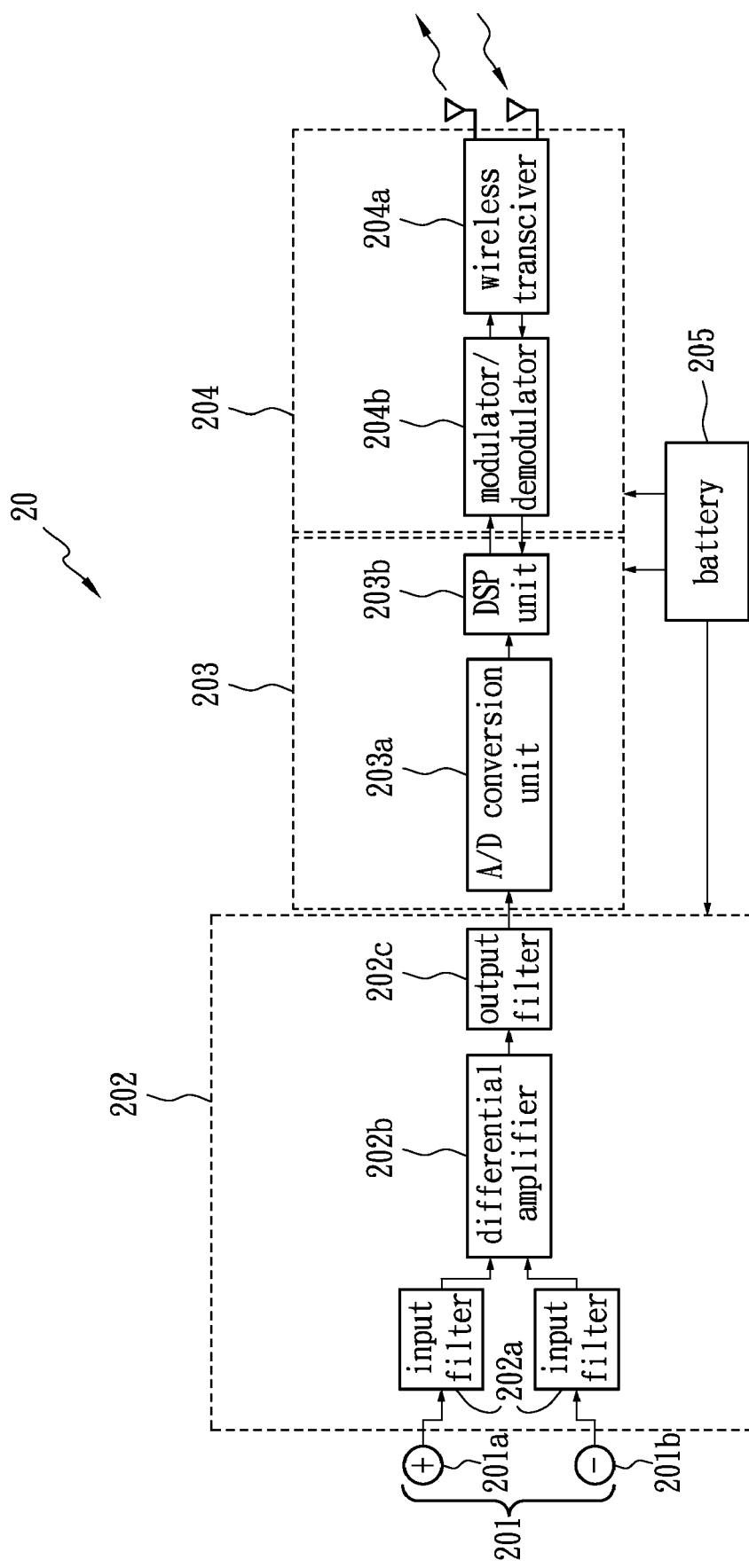
FIG. 2 shows a schematic view of a function block diagram of a miniature wireless apparatus for collecting physiological signals in accordance with a first embodiment of the present invention.

FIG. 2 shows a function block diagram of a miniature wireless apparatus 20 for collecting physiological signals in accordance with a first embodiment of the present invention. The miniature wireless apparatus 20 comprises an electrode pair 201, an amplifier module 202, a microcontroller 203, a wireless module 204 and a battery 205.

The electrode pair 201 is differential and comprises a positive electrode 201a and a negative electrode 201b, which are connected to a person under test to collect a pair of physiological signals. The physiological signals comprise an electroencephalogram (EEG) signal, an oculomotor signal, a forehead temperature signal, a body temperature signal, an electrocardiogram (ECG) signal, an electromyogram signal, and a narial breath or a breathing signal.

The amplifier module 202 comprises a pair of input filters 202a, a differential amplifier 202b, and an output filter 202c. The physiological signals collected from the positive electrode 201a and the negative electrode 201b have noise filtered out by the input filters 202a to increase the signal-to-noise ratio, and then the physiological signals are differentially amplified by the differential amplifier 202b.

The differential amplifier 202b attenuates the common mode noise of the pair of physiological signals, and simultaneously amplifies the differential part of the pair of physiological signals with appropriate magnification, so as to match the voltage range of the analog-to-digital conversion of the microcontroller 203.

The output filter 202c filters out an amplified physiological signal that is over the Nyquist frequency (i.e., twice the sampling frequency of the analog-to-digital conversion of the microcontroller 203). Moreover, the impedance of the input end of the amplifier module 202 is larger than 200 kilo Ohms, so as to prevent the leakage current caused by an operational error. The input filter 202a and the output stage filter 202c can be implemented by passive elements such as resistors or capacitors. The differential amplifier 202b can be implemented by an operational amplifier or an instrumentation amplifier of the integrated circuit.

The microcontroller 203 comprises an analog-to-digital conversion unit 203a and a digital signal processing unit 203b. The analog-to-digital conversion unit 203a performs an analog-to-digital conversion for the amplified physiological signal generated from the amplifier module 202 with the appropriate voltage resolution and sampling frequency, and then the digital signal processing unit 203b performs a data compression for a digital physiological signal generated by the analog-to-digital conversion unit.

The wireless module 204 comprises a wireless transceiver 204a and a modulator/demodulator 204b. The input end of the wireless module 204, being connected to the microcontroller 203, is a serial or parallel digital channel for receiving a digital physiological signal generated from the microcontroller 203. Then the modulator 204b modulates the digital physiological signal compressed by the digital signal processing unit 203b to a modulated physiological signal with the carrier frequency of 2.4 GHz. The modulated physiological signal is sent to a far end by the wireless transceiver 204a in the form of a wireless physiological signal. Meanwhile, the wireless transceiver 204a also receives a wireless signal from the far end, and then the wireless signal is demodulated by the demodulator 204b to a digital data signal, and the digital data signal is transmitted to the microcontroller 203 through the digital channel. The wireless signal sent from the far end comprises a control signal of the miniature wireless apparatus 20 and an acknowledgement signal sent by a receiver of the far end. The wireless module 204 performs wireless transmission and reception using the international industry, science, and medical (ISM) exclusive frequency band.

FIG. 3(a), FIG. 3(b), FIG. 3(c) and FIG. 3(d) show exploded schematic views of miniature apparatus in accordance with a first embodiment of the present invention.

Figure 3A:
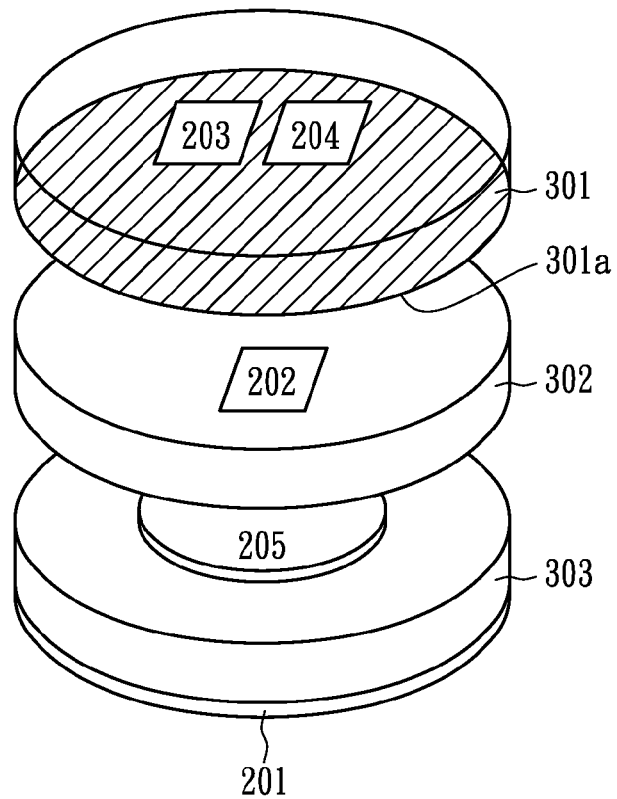
FIGS. 3(a), 3(b), 3(c) and 3(d) show exploded schematic views of the miniature apparatus in accordance with a first embodiment of the present invention.

The miniature apparatus shown in FIG. 3(a) is implemented by a structure of multilayered circuit boards, i.e., circuit boards 301, 302 and 303. Each of the circuit boards 301, 302 and 303 comprises an upper surface and a bottom surface. The microcontroller 203 and the wireless module 204 are disposed on the upper surface of the circuit board 301, the amplifier module 202 is disposed on the upper surface of the circuit board 302, the electrode pair 201 is disposed on the bottom surface of the circuit board 303, and the battery 205 is disposed on the upper surface of the circuit board 303 and is connected to the bottom surface of the circuit board 302. The wireless module 204 disposed on the upper surface of the circuit board 301 helps to transmit and receive wireless signals. An isolation ground plane 301a disposed on the bottom surface of the circuit board 301 helps to increase the signal-to-noise ratio of the amplifier module 202. The battery 205 can be disposed between the bottom surface of the circuit board 302 and the upper surface of the circuit board 303. The bottom surface of the second circuit board 302 is connected to the positive pole or the negative pole of the battery 205 and used as a power source layer, and the upper surface of the third circuit board 303 is connected to the other pole of the battery 205 and used as another power source layer.

Figure 3B:
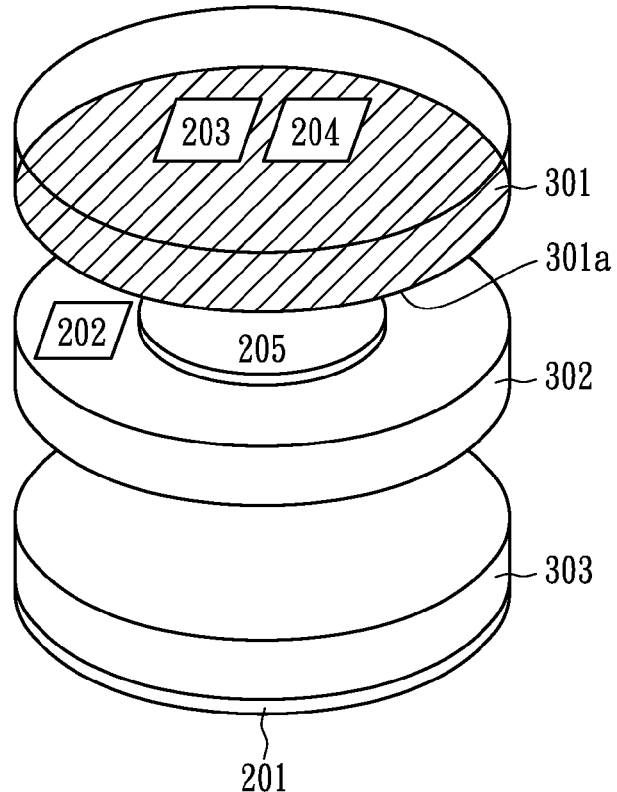

The battery 205 can also be disposed on the upper surface of the circuit board 302 and is connected to the bottom surface of the circuit board 301, as shown in FIG. 3(b).

Figure 3C:
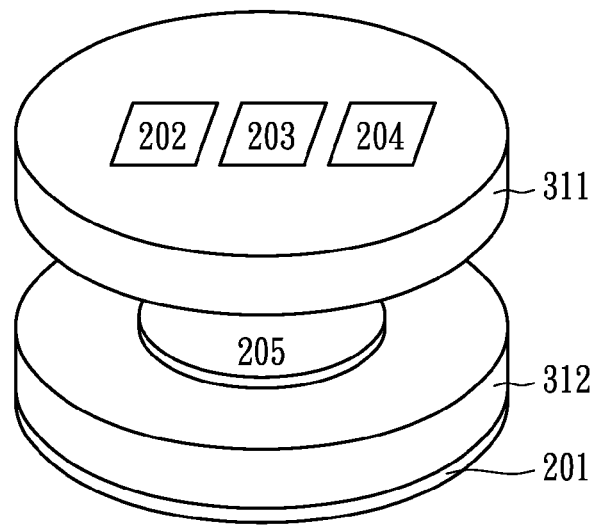
Figure 3D:
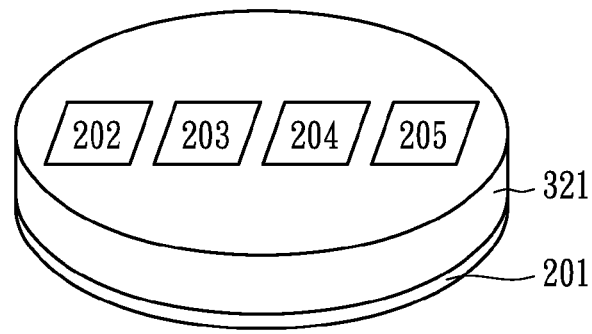
Figure 3E:
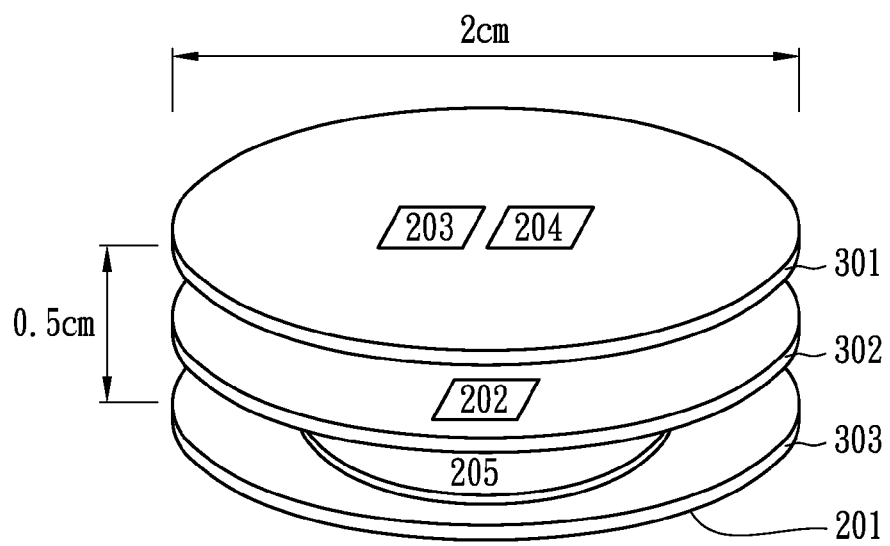
FIG. 3(e) is a perspective view of an actual structure of the miniature wireless apparatus for collecting physiological signals according to FIG. 3(a).

All circuit boards 301, 302 and 303 can be implemented in a miniature structure shown in FIG. 3(e), wherein the miniature structure has a diameter of 2 cm and a height of 0.5 cm.

As shown in FIG. 3(c), the amplifier module 202, the microcontroller 203 and the wireless module 204 can be disposed on the upper surface of a circuit board 311, the battery 205 is disposed on a circuit board 312, and the electrode pair 201 is disposed on the bottom surface of the circuit board 312.

As shown in FIG. 3(d), the amplifier module 202, the microcontroller 203, the wireless module 204 and the battery 205 can be disposed on the upper surface of a circuit board 321, and the electrode pair 201 is disposed on the bottom surface of the circuit board 321. The circuit board 321 and devices thereon can be implemented in a chip.

The allocation of the battery 205 in FIG. 3(a) or FIG. 3(c) not only prevents the electrode pair 201 from electromagnetic interference from the microcontroller 203 and the wireless module 204, but also lowers the center of gravity of the miniature apparatus 20. This helps to increase the connection stability between the person under test and the miniature apparatus 20.

Figure 4A:
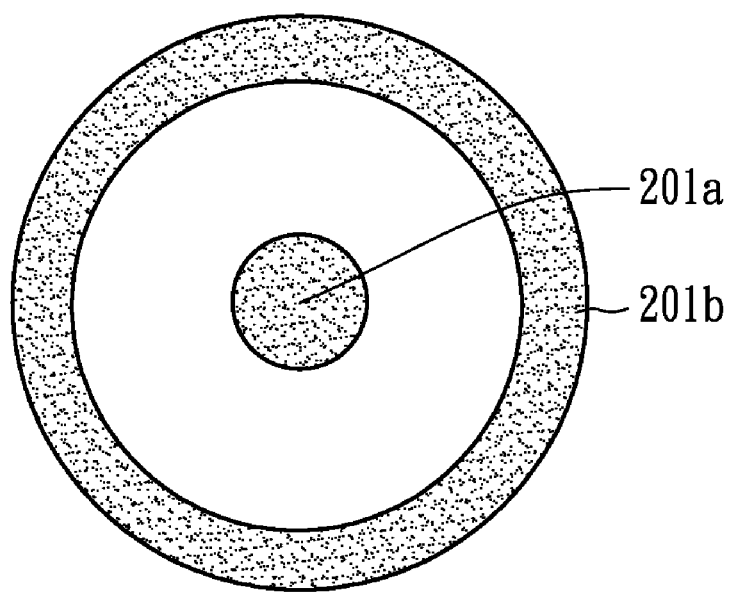
FIGS. 4(a) and 4(b) show top plan views of an electrode pair in accordance with the first embodiment of the present invention.
Figure 4B:
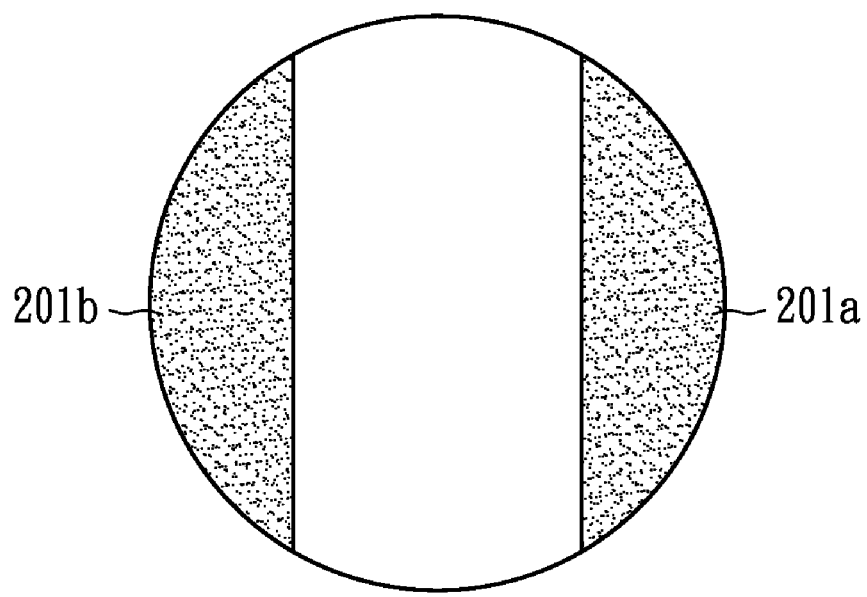

The electrode pair 201 is disposed on the bottom surface of the circuit board 303, 312 or 321 and can be implemented by a print circuit board (PCB) as shown in FIG. 4(a) or FIG. 4(b).

Figure 5:
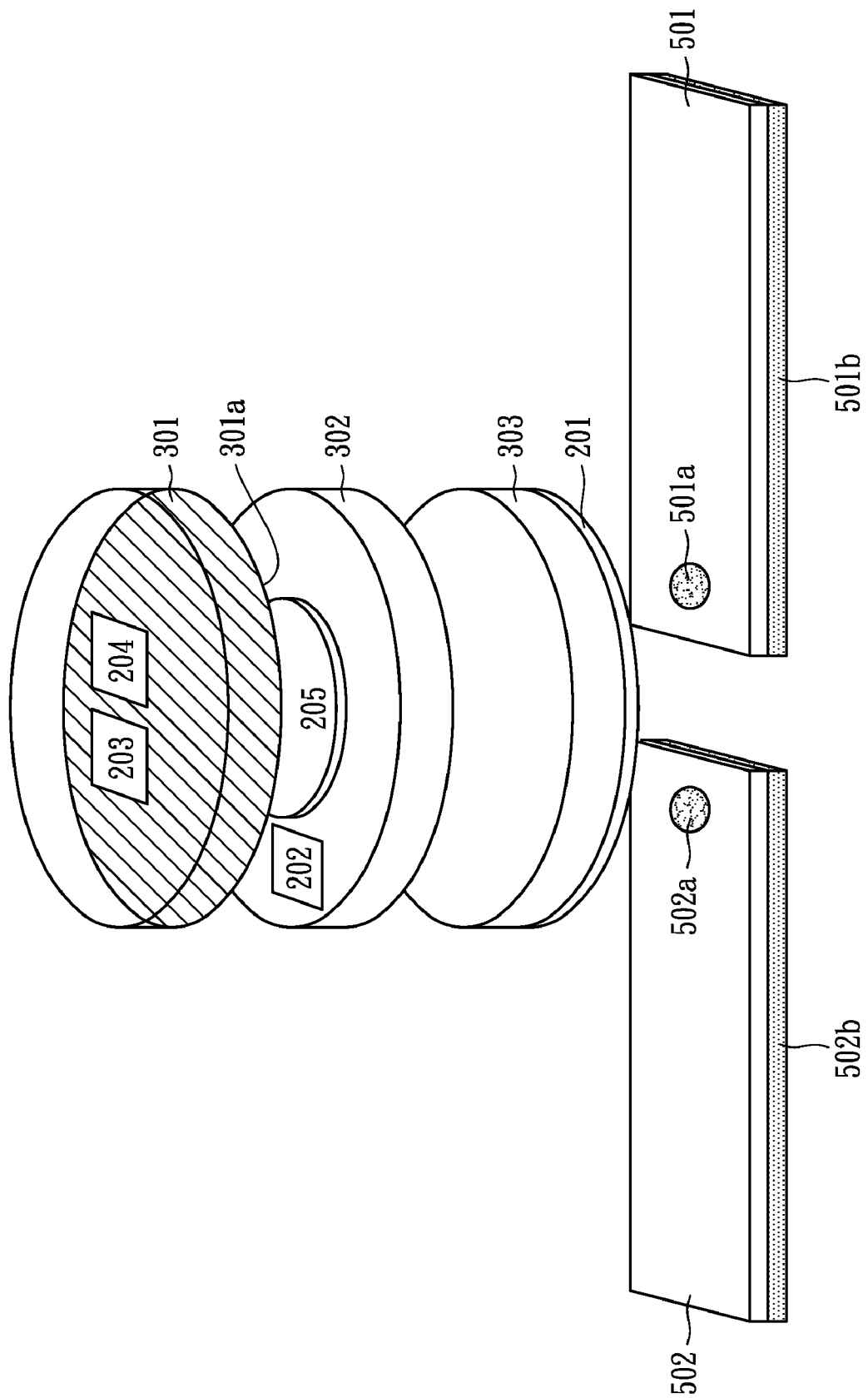
FIG. 5 shows an exploded schematic view of a miniature wireless apparatus in accordance with a second embodiment of the present invention.
Figure 6:
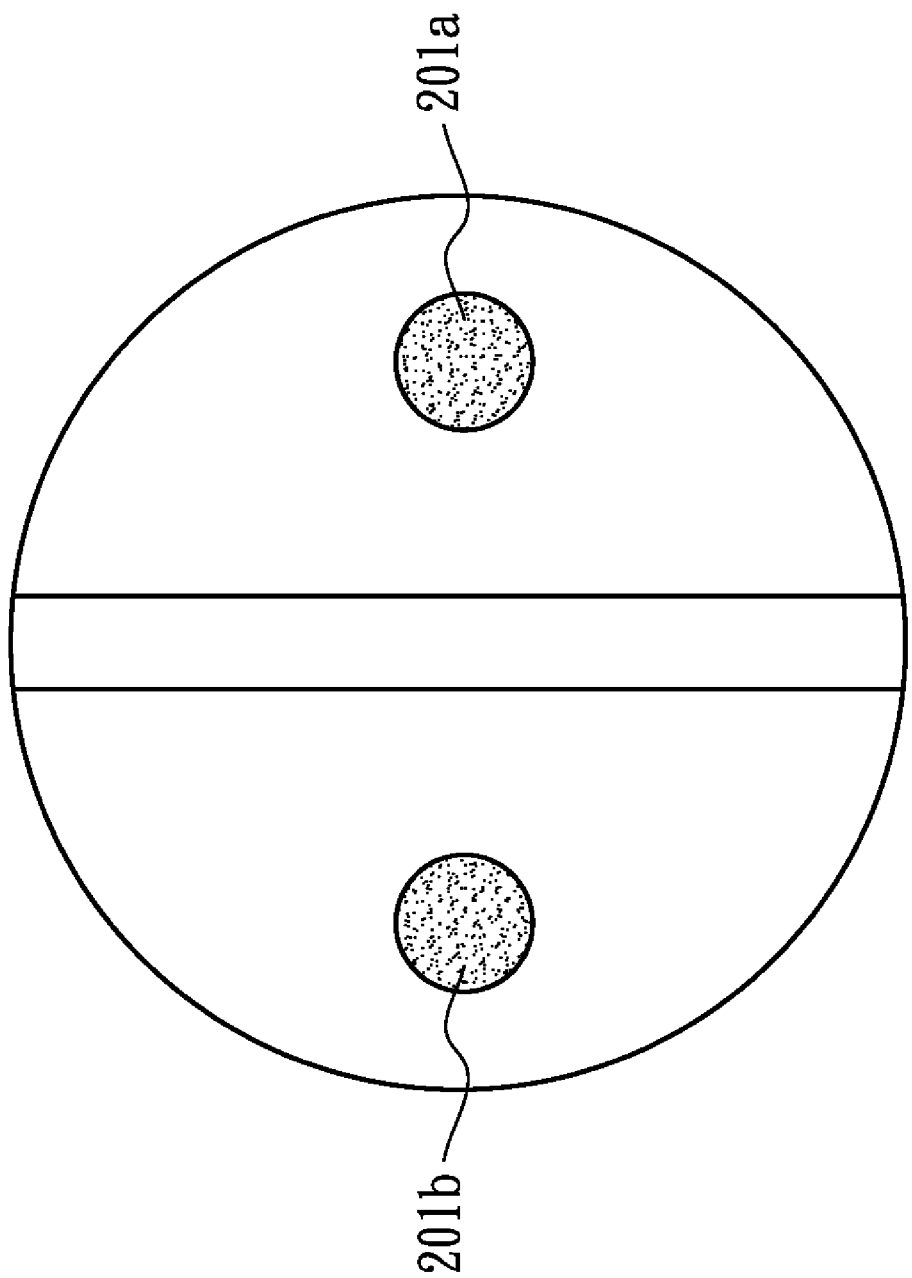
FIG. 6 shows a top view of an electrode pair in accordance with the second embodiment of the present invention.

FIG. 5 shows an exploded schematic view of a miniature wireless apparatus in accordance with a second embodiment of the present invention. Compared to the miniature apparatus of FIG. 3(b), two electrode patches 501 and 502 with electric contact points 501a and 502a are disposed under circuit board 303, respectively. The electrode patches 501 and 502 can be further connected to conductive films 501b and 502b respectively. The conductive films 501b and 502b can be designed with double-sided adhesive; one side is adhered to the electrode patch and the other side is adhered to the body surface of the person under test to generate the conductive contact, so as to collect the physiological signals. Since the conductive films 501b and 502b can be changed often, the skin inflammation of the person under test caused by long-term contact can be avoided. The conductive films 501b and 502b are connected electrically to the positive electrode 201a and the negative electrode 201b through the electric contact points 501a and 502a. The design of the electrode pair 201 of the bottom surface of the circuit board layer 303 on FIG. 5 is shown in FIG. 6.

The miniature wireless apparatus for collecting physiological signals can further comprise an outer waterproof film or an outer waterproof cover, such that the person under test feels free in doing various activities.

The above-described embodiments of the present invention are intended to be illustrative only. Numerous alternative embodiments may be devised by those skilled in the art without departing from the scope of the following claims.

We claim:

1. A miniature wireless apparatus for collecting physiological signals comprising:
    a first circuit board having an upper surface and a bottom surface;
    a second circuit board having an upper surface and a bottom surface;
    a third circuit board having an upper surface and a bottom surface, said second circuit board being positioned between said first circuit board and said third circuit board;
    an electrode pair disposed on said bottom of said third circuit board, said electrode pair comprising a positive electrode, said electrode pair suitable for connection to a person so as to collect a pair of the physiological signals;
    an amplifier module disposed on said upper surface of said second circuit board, said amplifier module suitable for amplifying the pair of physiological signals, said amplifier module having analog circuits therein;
    a microcontroller disposed on said upper surface of said first circuit board, said microcontroller suitable for performing an analog-to-digital conversion and a data compression for the amplified physiological signals generated by said amplifier module;
    a wireless module disposed on said upper surface of said first circuit board, said wireless module suitable for modulating the digital physiological signals generated by microcontroller and for transmitting the modulated digital physiological signals to a receiver;
    a battery disposed between said bottom surface of said second circuit board and said upper surface of said third circuit board, said battery having a positive pole and a negative pole; and
    an isolated ground plane formed on said bottom surface of said first circuit board, said isolated ground plane suitable for increasing a signal-to-noise ratio of said analog circuits of said amplifier module.

2. The miniature wireless apparatus of claim 1, said bottom surface of said second circuit board connected to one of said positive pole and said negative pole of said battery so as to be a power source layer, said upper surface of said third circuit board connected to the other of said positive pole and said negative pole of said battery so as to be another power source layer.

* * * * *